(12) United States Patent
Verdine et al.

(10) Patent No.: US 6,369,237 B1
(45) Date of Patent: Apr. 9, 2002

(54) DNA GLYCOSYLASE INHIBITORS, AND USES RELATED THERETO

(75) Inventors: Gregory L. Verdine, Lexington; Li Deng, Brookline, both of MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 08/812,653

(22) Filed: Mar. 7, 1997

(51) Int. Cl.[7] .................. C07D 207/00; C07H 21/04; C07H 19/00

(52) U.S. Cl. .................. 548/400; 536/24.3; 536/24.5; 536/26.7; 536/28.1; 536/22.1

(58) Field of Search .................. 536/24.3, 24.5, 536/26.7, 28.1; 547/400

(56) References Cited

U.S. PATENT DOCUMENTS

| | | |
|---|---|---|
| 4,861,759 A | 8/1989 | Mitsuya et al. |
| 5,681,941 A | 10/1997 | Cook et al. |

FOREIGN PATENT DOCUMENTS

| | | |
|---|---|---|
| EP | 0733630 A1 | 12/1994 |
| JP | 07002846 | 6/1993 |
| JP | 09020776 | 6/1995 |
| WO | WO 91/07180 | 5/1991 |

OTHER PUBLICATIONS

Wong et al., J. Organic Chem., vol. 60(6), p. 1498, 1995.*
Altmann et al. Chem. Abstr. vol. 124, No. 19, 1996, p. 1327, Abstr. No. 261558a, Angew Chem. 106:1735–1738, 1994.*
Wong et al. J. Org. Chem. 60:1492–1501, 1995.*
Yokoyama et al. J. Org Chem. 61:6079–6082, 1996.*
Huang et al. Synthesis Aug., 1993, p. 769–771.*
Rassu et al. Tetrahedron Letters, 35(23):4019–4022, 1994.*
Deng, L., et al., "Unusually Strong Binding of a Designed Transition–State Analog to a Base–Excision DNA Repair Protein", *J. Am. Chem. Soc.*, 119, pp. 7865–7866 (1997).
Porello, S.L., et al., "Specific Recognition of Substrate Analogs by the DNA Mismatch Repair Enzyme MutY", *J. Am. Chem. Soc.*, 118, pp. 10684–10692, (1996).
Argani, R., et al., "Herpes Simplex Virus Type 1 (HSV–1) Uracil–DNA Glycosylase: Functional Expression in *Escherichia coli*, Biochemical Characterization, and Selective Inhibition by 6–Ip–n–Octylanillino) Uracil", *Virology* 211, 307–311, (1995).
Botta, M., et al., "Researches on Antiviral Agents. 41. Studies on the chemistry of 6–Methyl–2–methoxy–4–O–acyloxy and 6–Methyl–2,4–di–O– acyloxypyrimidine Derivatives as New Acylation Reagents and Inhibitors of Uracil DNA Glycosylases", *Tetrahedron*, vol. 50, No. 11, 3603–3618, (1994).

Caradonna, S., et al., "Affinity Purification and Comparative Analysis of Two Distinct Human Uracil–DNA Glycosylases", *Experimental Cell Research*, 22, 345–359, Article No. 0044, (1996).

Focher, F., et al., "Herpes simplex virus type 1 uracil–DNA glycosylase: isolation and selective inhibition by novel uracil derivatives", *Biochem. J.*, 292, 883–889, (1993).

Karran, P., et al., "Specificity of the Bacteriophage PBS2 Induced Inhibitors of Uracil–DNA Glycosylase", *Biochemistry*, 20, 6092–6096, (1981).

Lundquist, A.J., et. al., "Site–directed Mutagenesis and Characterization of Uracil–DNA Glycosylase Inhibitor Protein", *The Journal of Biological Chemistry*, vol. 272, No. 34, Issue of Aug. 22, 21408–21419, (1997).

Mol, C.D., et al., "Crystal Structure of Human Uracil–DNA Glycosylase in Complex with a Protein Inhibitor: Protein Mimicry of DNA", *Cell*, vol. 82, Sep. 8, 1995, 701–708, (1995).

Scharer, O.D., et al., "A Designed Inhibitor of Base–Excision DNA Repair", *J. AM. Chem. Soc.*, 117, 10781–10782, (1995).

Scharer, O.D., et al., "Specific Binding of the DNA Repair Enzyme AlkA to a Pyrrolidine–Based Inhibitor", *J. Am. chem. Soc.*, 117, 6623–6624, (1995).

Scharer, O.D., et. al., "Investigation of the mechanisms of DNA binding of the human G/T glycosylase using designed inhibitors", *Proc. Natl. Acad. Sci. USA*, vol. 94, 4878–4883, May 1997.

Wang, Z., et. al., "Overproduction and characterization of the uracil–DNA glycosylase inhibitor of bacteriophage PBS2", *Gene*, 99, 31–37, (1991).

* cited by examiner

*Primary Examiner*—Gary Geist
*Assistant Examiner*—Howard V. Owens, Jr.
(74) *Attorney, Agent, or Firm*—Dana M. Gordon; Foley, Hoag & Eliot LLP

(57) ABSTRACT

The present invention pertains to novel inhibitors of DNA glycosylases. The invention is based at least in part on the observation that specific substituted pyrrolidines, and analogs thereof, are capable of specifically inhibiting DNA glycosylases, e.g., as transition state analogs, and consequently are useful for modulation of DNA repair. Such compounds can, for example, be used for treating subjects having a disorder associated with excessive cell proliferation, such as in the treatment of various cancers. Furthermore, these glycosylase inhibitors can be used as anti-bacterial, anti-viral and anti-fungal agents.

25 Claims, 4 Drawing Sheets

DNA GLYCOSYLASE INHIBITORS, AND USES RELATED THERETO

GOVERNMENT SUPPORT

Work described herein was supported by National Institutes of Health (Grant No. GM51330). The United States Government has certain rights in the invention.

BACKGROUND OF THE INVENTION

The role of DNA as a stable repository for genetic information is constantly challenged by the chemical reactivity of the DNA bases (Lindahl (1993) *Nature* 362:709–715). DNA molecules, like all other biomolecules, can be damaged in numerous ways. Nearly all atoms of the DNA bases are subject to some form of hydrolysis, oxidative damage or alkylation. Moreover, spontaneous damage due to replication errors, deamination, depurination and oxidation is compounded in the real world by the additional effects of radiation and environmental chemicals. If left uncorrected, these lesions can be lethal to a cell.

The "pathway" most commonly employed to remove incorrect bases (like uracil) or alkylated bases (like 3-methyladenine) or other damaged bases is called "base excision repair". Excision repair relies on the redundant information in the duplex to remove a damaged base or nucleotide and replace it with a normal base by using the complementary strand as a template. In base excision repair the removal of the lesion occurs in two steps: First, the damaged base is released by a DNA glycosylase, and then the abasic sugar (AP site) is excised by AP endonucleases. Each base excision reaction is of a limited substrate range because the DNA glycosylases that initiate the repair process are in intimate contact with the lesion during catalysis.

It is an object of the present invention to provide inhibitors of DNA glycosylases in order to, e.g., manipulate the DNA repair response of a cell.

SUMMARY OF THE INVENTION

One aspect of the present invention provides a DNA glycosylase inhibitor represented in the general formula (I), or a pharmaceutically acceptable salt thereof:

Formula I

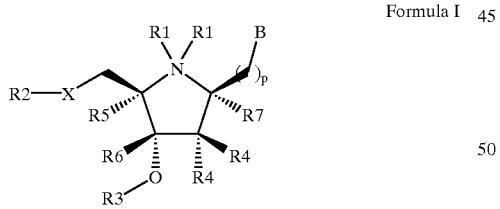

wherein,

B is a nucleoside purine or pyrimidiine base, or a heterocyclic analog thereof,

X is O, N, S or $CH_2$;

R1, independently for each occurence, is absent or is a hydrogen, or an amino protecting group;

R2 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—8, —$(CH_2)_m$—SH, —$(CH_2)_m$—S-lower alkenyl, —$(CH_2)_m$—S-lower alkenyl, —$(CH_2)_m$—S—$(CH_2)_n$—8, or a solid or polymeric support;

R3 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—8, —$(CH_2)_m$—SH, —$(CH_2)_m$—S-lower alkenyl, —$(CH_2)_m$—S-lower alkenyl, —$(CH_2)_m$—S—$(CH_2)_n$—R8, or a solid or polymeric support;

R4, R5, R6 and R7 are each, independently, as valence and stability permit, hydrogen, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—R8, —$(CH_2)_m$—SH, —$(CH_2)_m$—S-lower alkyl, —$(CH_2)_m$—S—$(CH_2)_n$—R8;

R8 is, independently for each occurrence, a substituted or unsubstituted aryl, aralkyl, cycloalkyl, cycloalkenyl or heterocycle, a carbonyl, a sulfonyl or a phosphoryl;

p is zero, 1 or 2, and n and m are independently for each occurrence zero or an integer in the range of 1 to 6, which compound inhibits an N-glycosidic activity of a DNA glycosylase.

In preferred embodiments, the subject inhibitor is represented in the general formula:

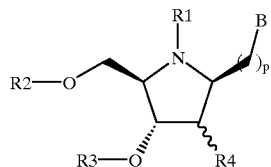

For example, the inhibitor is represented in the general formula:

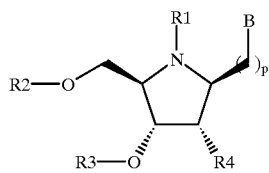

The subject inhibitor can be incorporated as part of an oligonucleotide, e.g., R2 and/or R3 are one or more nucleotides (including analogs). For istance, the nucleic acid can be at least 4, 8, 10, 15, 20, 30 or more nucleotide units in length.

In preferred embodiments, the subject compounds inhibit a DNA glycosylase which is a member of the EC category EC 3.2.2.-. For instance, the DNA glycosylase may be, e.g., a purine nucleosidase (EC 3.2.2.1), an inosine nucleosidase (EC 3.2.2.2), a uridine nucleosidase/uracil deglycosylase (EC 3.2.2.3), a ribosylpyrimidine nucleosidase (EC 3.2.2.8), an inosinate nucleosidase (EC 3.2.2.12), a 1-methyladenosine nucleosidase (3.2.2.13), a dna-deoxyinosine glycosidase (EC 3.2.2.15), a methylthioadenosine nucleosidase (EC 3.2.2.16), a DNA-3-methyladenine glycosidase (I) (EC 3.2.2.20), a DNA-3-methyladenine glycosidase (II) (EC 3.2.2.21), and a formamidopyrimidine-DNA glycosidase (EC 3.2.2.23). In certain embodiments, the the DNA glycosylase is a mammalian DNA glycosylase, such as MYH, Mpg, 3Mg, Ung1 and Ung2. In other embodiments, the DNA glycosylase is a bacterial DNA glycosylase such as MutM, MutT, fpg4 and MutY. In yet other embodiments, the DNA glycosylase is a viral DNA glycosylase from, e.g., an Epstein Barr Virus or Herpes Simplex Virus.

Another aspect of the present invention pertains to pharmaceutical preparations including the subject DNA glycosylase and a pharmaceutically acceptable carrier.

Another aspect of the present invention provides a solid support (or soluble polymeric support) derivatized with the subject DNA glycosylase.

Still another aspect of the present invention relates to a method for decreasing the DNA repair activity of a a cell comprising contacting the cell with one or more of the subject DNA glycosylase inhibitors. For instance, the subject method can be used for increasing the sensitivity of a cell to DNA damaging agents. It can be carried out on cells in culture, e.g., the glycosylase inhibitor is provided as a cell culture additive. Alternatively, it can be used in the treatment of an animal, e.g., the glycosylase inhibitor is administered to the animal as a therapeutic composition. In the instance of the latter, the glycosylase inhibitor can be administered as part of a treatment for a neoplastic conditions, such as in the treatment of leukemias, lymphomas, myelomas, medullomas, medulloblastomas, neuroblastomas, carcinomas, sarcomas and glioblastomas, neoplasias of breast tissue, neoplasias of testicular tissue, neoplasias of endometrial tissue, and neoplasias of testicular tissue, and the like.

In a preferred therapeutic method, the glycosylase inhibitor is contacted with the cell conjointly with a DNA damaging agent. For instance, the DNA damaging agent can include one or more compounds which as DNA alkylating agents and DNA intercalating agents. Exemplary DNA damaging agent include psoralens, tricyclic furocoumarins, dacarbazines, amsacrine, actinomycins, azaserine, bleomycin, carminomycin, daunomycins, mitomycins, mitoxantrones, plicamycins, haloethylnitrosoureas, sulfer mustard, nitrogen mustards, cis-diamminedichloro-platinum (II) (cisplatin), cis-diammino-(1,1-cyclobutanedicarboxylato)platinum(II) (carboplatin), cis-diammino-(1,2, -cyclohexyl)-dichloroplatinum(II), cis-(1,2-ethylene-diammine)dichloro-platinum(II), ethylenimines and methylmelamines. In other embodiments, the the DNA damaging agent can include DNA damaging electromagnetic radiation, e.g., ionizing radiation.

The subject method can also be used to inhibit the proliferation of: bacterial cells, e.g., in the treatment of septicemia; fungal cells, e.g., in the treatment of fungicemia; and/or virally-infected cells, e.g., for treating cells infected with a virus having an endogenous glycosylase activity.

Another aspect of the present invention provides a cell (or tissue), e.g., in cell culture, having an impaired DNA repair ability resulting from treatment of the cell with one or more of the subject glycosylase inhibitors. Such cells can be used to ascertain the mutagenic/carcinogenic potential of a chemical or environmental conditions, or can be used to ascertain the ability of a test agent to protect the cell against DNA damage by a known carcinogen/mutagen. In preferred embodiments, the cell is a mammalian cell, more preferably a human cell.

Another aspect of the present invention provides a method for isolating a DNA glycosylase comprising contacting a cytoplasmic preparation of a cell with a solid support (or soluble polymeric support) derivatived with an inhibitor of the present invention, then removing the solid support for contact with the cytoplasmic preparation in order to isolate any glycosylase enzyme bound to the inhibitor.

Yet another aspect of the present invention provides a kit for carrying out conjoint administeration of a glycosylase inhibitor and a DNA damaging agent comprising (i) a DNA damaging agent formulated in a pharmaceutical carrier, and (ii) one or more of the subjecy glycosylase inhibitors, formulated in a pharmaceutical carrier

BRIEF DESCRIPTION OF THE DRAWINGS OF THE INVENTION

DETAILED DESCRIPTION OF THE INVENTION

Figure 1:
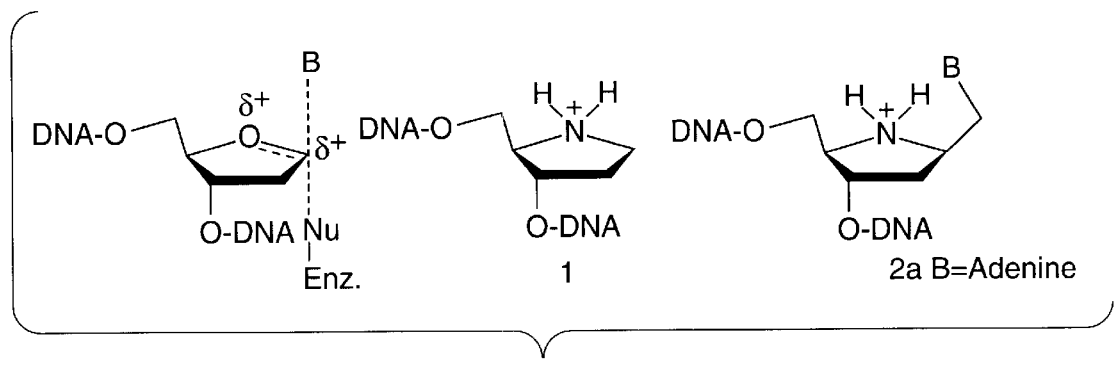
FIG. 1 depicts the analogy between the proposed transition state for enzyme-mediated glycosidic bind cleavage and the pyrrolidine ring of the subject inhibitors.

DNA repair enzymes, expressed in all organisms, maintain the integrity of genetic information through reconstitution of damaged DNA resulting from attacks by exogenous and endogenous agents as well as errors that arise during replication. The link between defective DNA repair and a variety of genetic diseases, including cancer, has been established. Furthermore, the art has also indicated the significance of DNA repair in regulating other critical biological events, such as progression through the cell cycle. Inhibitors of DNA repair enzymes offer an opportunity to manipulate the phenotypic and/or proliferative state of a cell.

The present invention pertains to novel inhibitors of DNA glycosylases. The invention is based at least in part on the observation that specific substituted pyrrolidines, and analogs thereof, are capable of specifically inhibiting DNA glycosylases, e.g., as transition state analogs, and consequently are useful for modulation of DNA repair. Such compounds can, for example, be used for treating subjects having a disorder associated with excessive cell proliferation, such as in the treatment of various cancers. Furthermore, these glycosylase inhibitors can be used as anti-bacterial, anti-viral and anti-fungal agents.

I. DEFINITIONS

Before further description of the invention, certain terms employed in the specification, examples, and appended claims are collected here.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formate, or a ketone), a thiocarbonyl (such as a thioester, a thioacetate, or a thioformate), an alkoxyl, a phosphoryl, a phosphonate, a phosphinate, anamino, an amido, an amidine, an imine, a cyano, a nitro, an azido, a sulfhydryl, an alkylthio, a sulfate, a sulfonate, sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "amino" is art recognized and refers to both unsubstituted and substituted amines, e.g., a moiety that can be represented by the general formula:

wherein $R_9$ and $R_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocyclyl or a polycyclyl; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

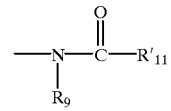

wherein R9 is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

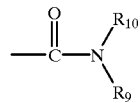

wherein $R_9$, $R_{10}$ are as defined above. Again, as will be appreciated in the art, preferred embodiments of the amide will not include imides which may be unstable.

The term "amidino", as used herein, refers to a moiety that can be represented by the general formula:

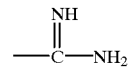

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

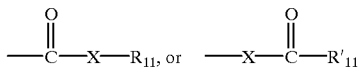

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$, is as defined above, the moiety is referred to herein as a carboxyl group, and particularly when R$_{11}$, is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

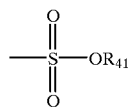

in which R$_{41}$ is an electron pair, hydrogen, alkyl, cycloalkyl, or aryl.

The term "sulfate" is art recognized and includes a moiety that can be represented by the general formula:

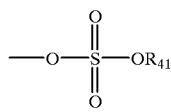

in which R$_{41}$ is as defined above.

The term "sulfonamido" is art recognized and includes a moiety that can be represented by the general formula:

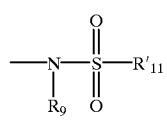

in which R$_9$ and R'$_{11}$ are as defined above.

The term "sulfamoyl" is art-recognized and includes a moiety that can be represented by the general formula:

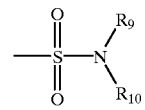

in which R$_9$ and R$_{10}$ are as defined above.

The term "sulfoxido", as used herein, refers to a moiety that can be represented by the general formula:

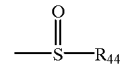

in which R$_{44}$ is selected from the group consisting of hydrogen, alkyl, alkenyl, alkynyl, cycloalkyl, heterocyclyl, aralkyl, or aryl.

A "phosphoryl" can in general be represented by the formula:

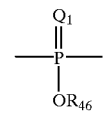

wherein Q$_1$, represented S or O, and R$_{46}$ represents hydrogen, a lower alkyl or an aryl. When used to substitute, e.g., an alkyl, the phosphoryl group of the phosphorylalkyl can be represented by the general formula:

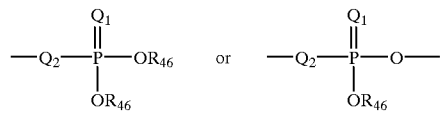

wherein Q$_1$ represented S or O, and each R$_{46}$ indepedently represents hydrogen, a lower alkyl or an aryl, Q$_2$ represents O, S or N. When Q$_1$, is an S, the phosphoryl moiety is a a "phosphorothioate".

A "phosphoramidite" can be represented in the general formula:

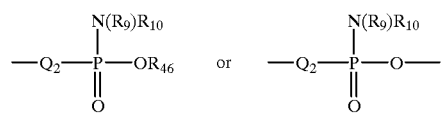

wherein R$_9$ and R$_{10}$ are as defined above, and Q$_2$ represents O, S or N.

A "phosphonarnidite" can be represented in the general formula:

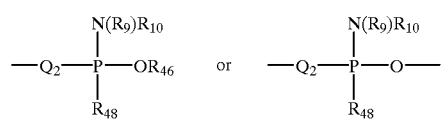

wherein R$_9$ and R$_{10}$ are as defined above, Q$_2$ represents O, S or N, and R$_{48}$ represents a lower alkyl or an aryl, Q$_2$ represents O, S or N.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulthydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like.

The terms "heterocyclyl" or "heterocyclic group" refer to 4- to 10-membered ring structures, more preferably 4- to 7-membered rings, which ring structures include one to four heteroatoms. Heterocyclyl groups include, for example, pyrrolidine, oxolane, thiolane, imidazole, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulthydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "solid support" refers to a material having a rigid or semi-rigid surface. Such materials will preferably take the form of small beads, pellets, disks, chips, dishes, multi-well plates, wafers or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

As used herein, "proliferating" and "proliferation" refer to cells undergoing mitosis.

The term "unwanted proliferation" refers to proliferation of cells which is undesired, be it due to transformation of the cells, e.g., neoplastic or hyperplastic, for purposes of wound healing, treatment of restenosis and other unwanted smooth muscle proliferation, cosmetic applications, etc.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

As used herein, "immortalized cells" refers to cells which have been altered via chemical and/or recombinant means such that the cells have the ability to grow through an indefinite number of divisions in culture.

A "patient" or "subject" to be treated by the subject method can mean either a human or non-human animal.

II. COMPOUNDS OF THE INVENTION

In the context of this disclosure, a "pyrrolidine-derived nucleoside" refers to a nitrogenous heterocyclic base linked to a pyrrolidine equivalent of a ribose or deoxyribose ring, or derivatives or analogs thereof. In general, the compounds of the present invention are derived from a pharmacophoric core of 2,3,5-substituted homopyrrolidine, or analogs thereof Preferred glycosylase inhibitors of the present invention include compounds of the general formula (Formula I) and pharmaceutically acceptable salts thereof

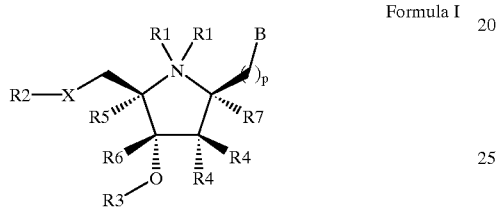

Formula I wherein,

B is a nucleoside purine or pyrimidiine base, or a heterocyclic analog thereof,

X is O, N, S or $CH_2$;

R1, independently for each occurence, is absent or is a hydrogen, or an amino protecting group;

R2 is a hydrogen, a nucleotide or oligonucleotide (e.g., 3' linked), a phosphoryl (such as a phosphate, e.g., mono-, di- or tri-ester), a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—R8, —$(CH_2)_m$—SH, —$(CH_2)_m$—S-lower alkyl, —$(CH_2)_m$—S-lower alkenyl, —$(CH_2)_m$—S—$(CH_2)_n$—R8, or a solid or polymeric support;

R3 is a hydrogen, a nucleotide or oligonucleotide (e.g., 5' linked), a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—R8, —$(CH_2)_m$—SH, —$(CH_2)_m$—S-lower alkyl, —$(CH_2)_m$—S-lower alkenyl, —$(CH_2)_m$—S—$(CH_2)_n$—R8, or a solid or polymeric support; and R4, R5, R6 and R7 are each, independently, as valence and stability permit, hydrogen, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—R8, —$(CH_2)_m$—SH, —$(CH_2)_m$—S-lower alkyl, —$(CH_2)_m$—S-lower alkenyl, —$(CH_2)_m$—S—$(CH_2)_n$—R8;

R8 is, independently for each occurrence, a substituted or unsubstituted aryl, aralkyl, cycloalkyl, cycloalkenyl or heterocycle, a carbonyl, a sulfonyl or a phosphoryl; and p is zero, 1 or 2;

n and m are independently for each occurrence zero or an integer in the range of 1 to 6.

As used herein, the definition of each expression, e.g. lower alkyl, m, etc., when it occurs more than once in any structure, is intended to be independent of its definition elsewhere in the same structure. In the instance of R2 and R3, it will be understood that X and O, respectively, can be considered part of a phosphoryl moiety or the like.

There is a wide range of substrate specificity amongst the glycosylase enzymes, e.g., with both broad and narrow specificities for various purine and pyrimidines. Accordingly, it will be appreciated that B can be derived from a purine or pyrmidine base, such as adenine, guanine, thymine, cytosine, uracil, or hypoxanthine, as well as any of a variety of other purine or pyrmidine base analogs. For instance, B can be selected from amongst such purine or pyrimidine derivatives as $N^7$-methylguaninie, 8-oxoguanine, $N^1,N^6$-ethinoadenine, $N^6$-benzoyladenine, $N^2$-isobutyrylguanine, $N^4$-benzoylcytosine, $N^6$-di-n-butylformamidinyladenine, $N^6$-(N-methyl-2-pyrrolidineamidinyl)-adenine, $N^6$-succinyladenine, $N^6$-phthaloyladenine, $N^6$-dimethylacetamidinyladenine, or $N^2$-di-n-butylformamidinylguanine, or an analog of a purine or pyrimidine base, such as purine, isocytosine, or xanthine (3,7-dihydro-1H-purine-2,6-dione), or their protected derivatives; or a substituted purine or pyrimidine base. Such substituents include, but are not limited to cyano, halo, haloalkyl, carboxy, formyl, hydroxy, alkoxy, aryl, azido, mercapto, nitro, carboxy esters, and carboxamides. Such bases include, but are not limited to, 6-chloropurine, 6-chloro-2-fluoropurine, 2,6-diaminopurine, 2-fluoro-$N^6$-hydroxyadenine, 2,6-dihydroxyaminopurine, 8-bromoadenine, 2-chloroadenine, 8-azidoadenine, 8-mercaptoadenine, 8-aminoadenine, 6-thioguanine, 2,6-dichloropurine, N,N-dimethyl-6-aminopurine, $N^6$-benzyladenine, 1,3-dimethylxanthine, 2-amino-6,8-dihydroxypurine, 6-methoxypurine, 6-mercaptopurine, 6-(2-hydroxyethyl)-aminopurine, $N^6$-(2-isopentyl)-adenine, $N^6$-furfuryladenine (kinetin), 5-bromomethyluracil, 5-dibromomethyluracil, 5-hydroxymethyluracil, 5-formyluracil, 5-fluorouracil, 5-bromouracil, 6-methyl-2-thiouracil, 5-hydroxymethyl-6-methyluracil, 5-hydroxyuracil (isobarbituric acid), 5-methoxyuracil, 5-methylcytosine, 5-trifluoromethyluracil, 5-nitrouracil, 5-aminouracil, 2-thiocytosine, 2-amino-4,6-dihydroxypyrimdine, 4-amino-2,6-dihydroxypyrimidine, 2-amino-4-hydroxy-6-methylpyrimidine, or 4-amino-6-hydroxy-2-mercaptopyrimidine, or their protected derivatives.

B may also be a nucleoside base analog; such analogs are molecules that mimic the normal purine or pyrimidine bases in that their structures (the kinds of atoms and their arrangement) are similar to the normal bases, but may either possess additional or lack certain of the functional properties of the normal bases; such base analogues include, but are not limited to, imidazole and its 2-,4-, and/or 5-substituted derivatives (substituents are as defined above), indole and its 2-,3-,4-,5-,6-, and/or 7-substituted derivatives, benzimidazole and its 2-,4-,5-, 6-and/or 7-substituted derivatives, indazole and its 3-,4-,5-,6-, and/or 7-substituted derivatives, pyrazole and 3-,4-, and/or 5-substituted derivatives, triazole and its 4 - and/or 5-substituted derivatives, tetrazole its 5-substituted derivatives, benzotriazole and its 4-,5-,6-, and/or 7-substituted derivative 8-azaadenine and its substituted derivatives, 8-azaguanine and its substituted derivatives, 6-azathymine and its substituted derivatives, 6-azauracil and its substituted derivatives, 5-azacytosine and its substituted derivatives, 8-azahypoxanthine and its substituted derivatives, pyrazolopyrimidine and its substituted derivatives, 3-deazauracil, orotic acid (2,6-dioxo-1,2,3,6-tetrahydro-4-pyrimidine carboxylic acid), barbituric acid, uric acid, ethenoadenine, and allopurinol (4-hydroxypyrazolo [3,4-d]pyrimidine), or their protected derivatives.

B can also be a "C-nucleoside", in which the normal C-N bond between the base and C-1' of the pyrrolidine is replaced by a C-C bond; such bases include, but are not limited to, uracil (in the C-nucleoside pseudouridine), 1-methyluracil, 1,3-dimethyluracil, 5(4)-carbomethoxy-1,2,3-triazole, 5(4)-carboxamido- 1,2,3-triazole, 3(5)-carboxymethylpyrazole, 3(5)-carbomethoxypyrazole, 5-carboethoxy-1-methylpyrazole, maleimide (in the C-nucleoside showdomycin), and 3(4)-carboxamido-4(3)-hydroxypyrazole (in the C-nucleoside pyrazomycin), or their protected derivatives.

Illustrative examples of amino protecting groups from which R1 can be chosen include: (a) aromatic urethane-type groups, such as fluorenylmethyloxycarbonyl (Fmoc), Cbz, and substituted benzyloxycarbonyl, such as, for example, p-chlorobenzyloxycarbonyl, p-bromobenzyloxycarbonyl, p-nitrobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type groups such as Boc, t-amyloxycarbonyl, isopropyloxycarbonyl, 2-(p-biphenylyl) isopropyloxycarbonyl, allyloxycarbonyl, and the like; (c) cycloalkyl urethane-type groups such as cyclopentyloxycarbonyl, cyclohexyloxycarbonyl, cycloheptyloxycarbonyl, adamantyloxycarbonyl, and the like.

In certain embodiments, R2 and/or R3, as well as are any of a variety of organic moieties. It is anticipated that the nucleoside-derived homopyrrolidine will serve as a pharmacophoric core structure, and that derivatives at other ring positions can effect the Ki and specificity of the particular inhibitor. As with other subsitutions, combinatorial libraries of various R2 and R3 substituents can be generated by parallel synthesis and rapidly tested (see below). Various deconvolution techniques are available for ascertaining, amongst the various ring positions, which changes that effect inhibitor efficacy are independent of other changes in the structure, and which are interdependent.

Where R2 and/or R3 is a hydroxyl-protecting group, it may be, for example, a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,3-dimethoxybenzyl group, an o-nitrobenzyl group, a p-nitrobenzyl group or a trityl group; or an acyl group such as a formyl group or an acetyl group. Particularly preferred is a methoxymethyl group, a tetrahydropyranyl group, a trityl group, a tert-butyldimethylsilyl group or an acetyl group.

It will be understood that the "oligonucleotide" which may be attached as either R2 or R3 refers generically to polydeoxynucleotides, polyribonucleotides, and to any other type of polynucleotide which is an N-glycoside of a purine or pyrimidine base or their equivalents. Such oligonucleotides may have internucleotide modifications such as uncharged linkages (e.g., methyl phosphonates, phosphotriesters, phosphoramidates, carbamates and the like) or charged linkers (e.g., phosphorothioates, phosphorodithioates and the like), as well as to other polymers containing nonnucleotide backbones (such as peptide-nucleic acids), providing that the polymers contain nucleoside bases in a configuration which allows the subject inhibitor to interact with a glycosylase.

In preferred embodiments, the subject glycosylase inhibitor is a compound represented in the general formula (Formula II)

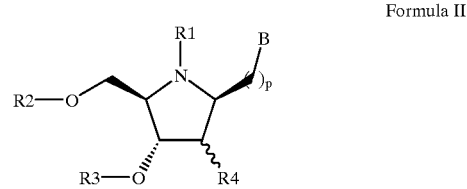

Formula II wherein each of B, p and R1–R4 are as defined above.

In still more preferred embodiments, the subject glycosylase inhibitor is a compound represented in the general formula (Formula III)

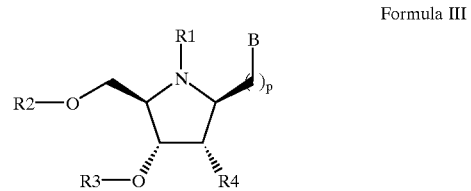

Formula III wherein each of B, p and R1 –R4 are as defined above.

In preferred embodiments, R4, R5, R6 and R7 are each, independently, hydrogen, —OH, —F, —OCH$_3$, —OC$_2$H$_5$, —OC$_3$H$_7$, —SCH$_3$, —SC$_2$H$_5$, —SC$_3$H$_7$, —OC$_3$H$_5$ —SC$_3$H$_5$. In preferred embodiments, R4 is a hydrogen, or a protected or unprotected hydroxyl group. In preferred embodiments, p is 1 or 2, though in even more preferred embodiments, p is 1. In preferred embodiments, R4 is not a hydroxyl or alkoxyl group, e.g., it is preferably hydrogen.

Certain compounds of the present invention may exist in particular geometric or stereoisomeric forms, e.g., in a substituent. The present invention contemplates all such isomers, including cis- and trans-isomers, R- and S-enantiomers, diastereomers, the racemic mixtures thereof, and other mixtures thereof, as falling within the scope of the invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the subject compound which contain a basic or acid moiety by conventional chemical methods. Generally, the salts are prepared by reacting the free base or acid with stoichiometric amounts or with an excess of the desired salt-forming inorganic or organic acid or base in a suitable solvent.

Contemplated equivalents of the compounds described in Formula I–III include compounds which otherwise correspond thereto, and which have the same general properties thereof, e.g. the ability to inhibit the activity of a DNA glycosylase, wherein one or more simple variations of substituents are made which do not adversely affect the efficacy of the compound in inhibiting the activity of the glycosylase.

Specificity of the various base excision repair pathways is conferred by the DNA N-glycoslyases. As described above, these enzymes hydrolyze the N-glycosylic bond between the base and the deoxyribose. A large number of DNA N-glycosylases have been identified. Most are small (<50 kd), monomeric enzymes with no known cofactor or divalent cation requirement. Most are highly specific for a certain type of altered base, but some have more relaxed specificity. The DNA N-glycosylases characterized to date include enzymes that recognize: uracil; hydroxymethyl uracil; 8-oxoguanine, 5-Methyl cytosine; hypoxanthine; thymine in G-T mispairs; adenine in G-A mispairs; 3-Methyl adenine; formamidopyrimidine (result of purine oxidation); and thymine glycol These enzymes have been best characterized in $E.$ $coli$, but in most cases similar activities have been detected in extracts of eukaryotic cells. Several of the $E.$ $Coli$ and eukaryotic enzymes have been cloned, and the glycosylase activity can be reconstituted in vitro. For instance, cloned uracil DNA glycosylases from all organisms are very similar. The human and $E.$ $coli$ genes are about 50% identical. By choice of particular substituents to the pyrrolidine ring, particularly the nucleoside base B, the subject compounds can be used to inhibit a wide range of glycosylases.

In preferred embodiments, the subject compounds inhibit DNA glycosylases categorized by the Enzyme Convention (EC) in the group EC 3.2.2. -, e.g., which hydrolyze N-glycosyl nucleic acids. For instance, the subject compounds can be selected on the basis of inhibiting a purine nucleosidase (EC 3.2.2.1), an inosine nucleosidase (EC 3.2.2.2), a uridine nucleosidase/uracil deglycosylase (EC 3.2.2.3), a ribosylpyrimidine nucleosidase (EC 3.2.2.8), an inosinate nucleosidase (EC 3.2.2.12), a 1-methyladenosine nucleosidase (3.2.2.13), a dna-deoxyinosine glycosidase (EC 3.2.2.15), a methylthioadenosine nucleosidase (EC 3.2.2.16), a DNA-3-methyladenine glycosidase (I) (EC 3.2.2.20), a DNA-3-methyladenine glycosidase (II) (EC 3.2.2.21), and/or a formamidopyrimidine-DNA glycosidase (EC 3.2.2.23). In certain embodiments, the subject inhibitors are more potent inhibitors of DNA glycosylases than of RNA N-glycosidases, e.g., by at least 1, 2 or 3 orders of magnitude.

A preferred class of DNA glyosylases upon which the subject inhibitors can act are characterized as nonredox 4Fe-4S proteins, such as represented by adenine glycosylase. The native 4Fe-4S cluster is ligated by four cysteine residues, is not sensitive to oxygen, and appears to maintain the structure of the protein domain to which it is bound.

Exemplary DNA glycosylases for which the subject compounds can function as inhibitors include: the bacterial glycosylases MutM, MutT, MutY, and homologs thereof from other organisms; as well as such mammalian glycosylases as MYH (the mammalian homolog of MutY, e.g., human MYH GenBank U63329), Mpg, 3Mg, Ung1, Ung2 and the like; and yeast glycosylases such as Ung, Mag, Ogg1 and the like. The subject inhibitors can also be selected on the basis of inhibiting a viral DNA glycosylase, such as are known for such viruses as the Epstein Barr Viruses (EBV) and Herpes Simplex Viruses (HSV), e.g., uracil glycosylase (ung).

The efficacy of any of the subject compounds in inhibiting the activity of a glycosylase can be determined by several methods known in the art, such as the gel mobility shift assay described in the appended examples, or such assays as described in Manuel et al. (1995) $J$ $Biol$ $Chem$ 10; 270:2652–2661; Maccubbin et al. (1994) $Cancer$ $Biochem$ $Biophys$ 14:183–191; Morgan et al. (1988) $Biochem$ $Cell$ $Biol$ 66:157–160; Seal et al. (1987) $Biochim$ $Biophys$ $Acta$ 925:226–233; and Evans et al. (1984) $Can$ $J$ $Biochem$ $Cell$ $Biol$ 62:1275–1282. For instance, in one assay format a compound can be assessed for its ability to inhibit a glycosylase activity by combining the compound with the glycosylase and a suitable substrates for the glycosylase activity. The resulting combination is maintained under conditions appropriate for the glycosylase to act upon the substrate. The extent to which the substrate is converted to product in the presence of the compound is compared with the extent of substrate conversion in the absence of the compound.

For example, in one embodiment the assay uses a synthetic substrate such as ultraviolet (UV) or chemically modified covalently closed circular (CCC) DNA to score for glycosylase activity. As described by Evans et al., supra, ethidium fluorescence can be used as a probe whereby the the topological properties of CCC DNA can be used as a reporter for glycosylase activity. The formation of AP sites by the activity of a glycosylase can be scored by monitoring changes in the conformation of the CCC DNA, and the inhibitory potency of each of the subject compounds towards the particular glycosylase being tested can be easily monitored in this assay.

Another convenient assay for assessing the activity of the subject compounds is illustrated by Labahn et al. (1996) $Cell$ 86:321–329. In this assay format, DNA labeled in its purine or pyrminidine bases (as appropriate) is admixed with the target glycosylase and the test compound. After some period of time, the reaction is stopped and the DNA precipitated. The label remaining behind in the supernatant, e.g., from solube bases released from the DNA by the activity of the glycosylase, is quantitated and compared to the same reaction lacking the test compound.

Still other assay formats can rely simply on detecting binding of the test compound with the glycosylase. For instance, the appended examples illustrate the use of a gel shift assay to detect the binding of an oligonucleotide including the subject pyrrolidine nucleotide analogs. In other embodiment, simple competitive binding assays can be carried out to screen for potential glycosylase inhibitors.

It will be apparent that such methods as described above can be carried out as rapid microtitre plate assay format to test a variety of potential inhibitors, e.g., which may generated by combinatorial chemistry. Thus, as described in more detail below, libraries in the order of hundreds of thousands of potential glycosylase inhibitors can be synthesized in parallel and rapidly screened.

In any of the above assay formats, suitable controls for selectivity can be provided. For refinement of the specificity of an inhibitor, other glycosylases can be used as counter screens. Thus, compounds within the scope of the invention include those which inhibit a glycosylase in a specific manner, e.g., as between glycosylases from different organisms and/or between different isoforms. For example, the subject inhibitors can be selected based on an ability to inhibit an adenine glycosylase without substantially inhibiting a uracil glycosylase.

It will also be apparent that differential screening assays can be used to select for those compounds of the present invention with specificity for non-human glycosylase enzymes. Thus, compounds which act specifically on pathogens, e.g., are antibacterial, antifungal or anti-parasitic agents, can be selected from the subject inhibitors. To illustrate, inhibitors of a bacterial glycosylase, such as MutY, can be used in the treatment of bacterial infections. When selecting an appropriate MutY inhibitor, human adenine glycosylases, such as MYH, can be used as counterscreens. In this manner, glycosylase inhibitors can be selected which, for example, have Ki's for inhibition of the bacterial enzyme which are orders of magnitude less than for the equivalent human enzyme.

The subject glycosylase inhibitors of the invention can be synthesized according to a variety of methods which will be apparent to those skilled in the art in light of the present disclosure.

Furthermore, Applicants note that a variety of techniques are available in the art for generating combinatorial libraries of small organic molecules such as the subject glycosylase inhibitors. Indeed, as will be evident from inspection of the synthetic scheme illustrated in the appended examples (see also FIG. 3) the modular synthesis of the subject glycosylase inhibitors lends itself well to combinatorial synthesis approaches. For exemplary combinatorial approaches which can be readily adapted to the subject compounds, see Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) JACS 115:252; PCT publications WO92/10092, WO093/09668 and WO91/07087; and the Lerner et al. PCT publication WO93/20242). Accordingly, a variety of libraries on the order of about 100 to 100,000 or more diversomers of the subject compounds can be synthesized, and, by use of a high throughput assay for detecting glycosylase inhibitors, such as described above and in the appended examples, rapidly screened for biological activity.

In an exemplary embodiment, a library of substituted diversomers can be synthesized according to the techniques described herein and the Still et al. PCT publication WO 94/08051, being linked to a polymer bead by a hydrolyzable or photolyzable group e.g., located at one of the positions of the pyrrolidine ring. According to the Still et al. technique, the library is synthesized on a set of beads, each bead including a set of tags identifying the particular diversomer on that bead. The beads can be dispersed on the surface of a permeable membrane, and the diversomers released from the beads by lysis of the bead linker. The diversomer from each bead will diffuse across the membrane to an assay zone, where it will interact with a glycosylase assay. For instance, a glycosylase can be immobilized or otherwise doped into the membrane. A substrate for the glycosylase is also added to the membrane. A diversomer from the library which is capable of inhibiting glycosylase-mediated hydrolysis of the substrate will be scored for by a zone around its bead which lacks product formation. Such beads can be picked, with the size of the labeling exclusion zone optionally being used to semi-quantitively rank activity, and the encoding tags on the bead used to identify the particular diversomer(s) of interest (e.g., see Still et al., supra).

In another exemplary embodiment, the diversomer library is easily assayed for glycosylase binding by "on-bead" detection techniques. Basically any means for detecting a glycosylase protein bound to the a bead can be used. For example, a labeled glycosylase can be contacted with a bead-derived library of diversomers on the basis of detecting labeled glycosylase which becomes associated with those beads displaying appropriate inhibitors. To illustrate, FITC-labeled glycosylase can be detected on beads by fluorescence-based techniques. Similarly, a biotinylated glycosylase can be detected on the beads by the use of streptavidin-labeled alkaline phosphatase and its substrate (e.g. p-nitrophenylphosphate).

III. EXEMPLARY USES

The subject glycosylase inhibitors are useful in a wide variety of applications due to their ability to alter the DNA repair response of a cell.

In one embodiment, the subject inhibitors can be used to inhibit proliferation of cells, such as by causing cell-cycle arrest or cell death (including apoptosis in eukaryotic cells). For instance, the subject inhibitors can be used to inhibit proliferation of mammalian cells, especially human cells, e.g., in the treatment of disorders marked by unwanted cell proliferation. In other embodiments, the subject inhibitors can be selected for use in the treatment of septicemias or fungicemias. In yet other embodiments, the glycosylase inhibitors can be used in the treatment of viral infection. They can also be used in agricultural applications, e.g., for defoliation and other crop control, as well as in insecticidal preparations.

In an exemplary embodiment, the subject DNA glyocsylase inhibitors can be used alone, or in conjunction with other agents, in the treatment of unwanted cell proliferation, such as may be due to transformation of the cells, e.g., neoplastic or hyperplastic, or for purposes of wound healing, treatment of restenosis and other unwanted smooth muscle proliferation, cosmetic applications, etc. For example, the subject method can be used in the treatment of sarcomas, carcinomas and/or leukemias. Exemplary disorders for which the subject method may be used as part of a treatment regimen include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The subject inhibitors can be combined with other therapeutics, e.g., such as cell cycle inhibitors, agents which promote apoptosis, agents which strengthen the immune response, and/or RxR agonists. Some of the co-administered therapeutics, particular those with cytotoxic effects or which lack specficity for the treated cells, may be given in smaller doses due to an additive, and sometimes synergistic effect with the glycosylase inhibitor.

In a preferred embodiment, the subject inhibitor is administered in conjunction with a DNA damaging agent. There are now almost 100 cytotoxic drugs licensed for use in cancer therapy in the United States. For certain malignancies such as childhood cancers, haematological malignancies, and germ cell tumors chemotherapy has been pivotal to the substantial improvement in therapeutic outcome achieved over the past 10 years. In contrast, improvements in the systemic management of adult solid tumors have been less dramatic. There is a clear and urgent need for new, more effective drugs for lung, breast, and colorectal malignancies. Improved systemic treatment could be achieved by modulating the activity of currently available drugs. This approach includes the development of effective drugs to control drug resistance. Accordingly, in one embodiment, the subject glycosylase inhibitors can be employed to enhance the anti-proliferative effect of a DNA damaging agent (also referred to herein as a "genotoxic agent").

A wide variety of chemotherapeutic agents work by initiating DNA damage. Cell death in response to DNA damage in most instances has been shown to result from apoptosis. However, the efficacy for cancer therapy by DNA damaging agents, such as radiation or chemotherapeutics (e.g., cisplatin or methotrexate) is often limited by the development of resistance. Biochemistry and tissue culture studies indicate that such resistance is a function of the capacity of cancer cells to repair damaged DNA. For instance, the art demonstrates enhanced expression of DNA repair enzymes by DNA resistant phenotypes of certain human carcinoma cell lines. See, e.g., Lai et al., (1988) *Biochem. Pharmacol.* 37:4597–4600; Hospers et al. (1988) *Cancer Res.* 48:6803–6807; Masuda et al., (1988) *Cancer Res.* 48:5713–5716; Kraker et al., (1988) *Cancer Lett.* 38:307–314; and Scanlon et al., (1989) *Anticancer Res.* 9:1301–1312.

According to the present invention, there is provided a method for increasing the sensitivity of a cell to a DNA damaging agent comprising co-administering to the cell, a DNA damaging agent (including radiation) along with a glycosylase inhibitor represented by Formula I. The terms "co-administered" and "in combination" in this context means that the drugs/radiation treatments are given substantially contemporaneously, either simultaneously or sequentially. If given sequentially, at the onset of administration of the glycosylase inhibitor, the DNA damaging agent is preferably still detectable at effective concentrations at the site of treatment, or DNA repair has not been substantially completed by the treated cell.

Another aspect of the present invention accordingly relates to kits for carrying out the conjoint administeration of the subject glycosylase inhibitors with DNA damaging compounds. In one embodiment, the kit comprises a glycosylase inhibitor formulated in a pharmaceutical carrier, and at least one DNA damaging agent, formulated with the glycosylase inhibitor or, as appropriate, in one or more separate pharmaceutical preparations.

The subject method can also be used to selectively kill cells in a heterogenous cell population, e.g., comprised of cells of two or more phylogenetically different species of organisms.

In the present method, a wide range of DNA damaging agents (or "genotoxic" agents) are available in the art. Many of these drugs currently are used to treat infections and neoplastic diseases in mammals, e.g., humans. For instance, two general classes of compounds that are suitable for use as the genotoxic agent in the present method include DNA alkylating agents and DNA intercalating agents.

In certain embodiments, the genotoxic agent can be a precursor that becomes reactive with cellular DNA spontaneously or following exposure to an activating stimulus, such as an enzyme, metabolite, ionizing or non-ionizing radiation, etc. For example, the genotoxic agent can be photoactivated. One class of photoactivatable compounds are the psoralens, derivatives of the tricyclic furocoumarin that produce pyrimidine base adducts. Thus, for example, trimethylpsoralen can be used in the subject method. Another class of photoactivatable genotoxic agents is represented by the dacarbazines.

Another general class of genotoxic agents, members of which can alkylate or intercalate DNA, includes synthetic and naturally occurring antibiotics. Of particular interest herein are antineoplastic antibiotics, which include but are not limited to the following classes of compounds: amsacrine; actinomycin A, C, D or F; azaserine; bleomycin; carminomycin; daunomycin or 14-hydroxydaunomycin; mitomycin A, B or C; mitoxantrone; plicamycin; and the like. Neoplasias currently managed by the foregoing, e.g., for which the conjoint treatment with a glycosylase inhibitor are preferred, include leukemias, lymphomas, myelomas, neuroblastomas, neoplasias of bladder, testicular, edometrial, gastric, or lung origin.

Still another general class of genotoxic agents, members of which alkylate DNA, includes the haloethylnitrosoureas, especially the chloroethylnitrosoureas. Representative members of this class include carmustine, chlorozotocin, fotemustine, lomustine, nimustine, ranimustine and streptozotocin. Neoplasias currently managed by the foregoing and particularly amenableto the subject method, include Hodgkin's, non-Hodgkin's and Burkitt's lymphomas, myelomas, glioblastomas and medulloblastomas, pancreatic islet cell carcinomas, small cell lung carcinomas and the like.

Yet another general class of genotoxic agents, members of which alkylate DNA, includes the sulfer and nitrogen mustards. These compounds damage DNA primarily by forming covalent adducts at the N7 atom of guanine. Representative members inlcude chlorambucil, cyclophosphamide, ifosfamide, melphalan, mechloroethamine, novembicine, trofosfamide and the like. Based on current therapeutic use of these compounds, the subject glycosylase inhibitors are combined with sulfer and nitrogen mustards in the treatment of, preferably, Hodgkin's, non-Hodgkin's and Burkitt's and other lymphomas, leukemias, myelomas, medullomas, neuroblastomas, small cell lung carcinomas, osteogenic sarcoma, neoplasias of breast, endometrial and testicular tissue, and the like.

Another class of genotoxic agents, the members of which form covalent DNA adducts, include heavy metal coordination compounds, including platinum compounds. Generally, these compounds form covalent interactions to DNA to form, e.g., cis-1,2-intrastrand dinucleotide adducts. Exemplary members of this group include cis-diamminedichloroplatinum(II) (cisplatin), cis-diammino-(1,1-cyclobutanedicarboxylato)platinum(II) (carboplatin), cis-diammino-(1,2, -cyclohexyl)-dichloroplatinum(II), and cis-(1,2-ethylene-diammine)dichloroplatinum(II). Neoplastic conditions treated with such genotoxic agents, e.g., and particularly amenable to the subject conjoint therapy, include testicular, endometrial, cervical, gastric, squamous cell, adrenocortical and small cell lung carcinomas, as well as medulloblastomas and neuroblastomas.

Still other classes of genotoxic agents which can be used in the subject conjoint method include DNA alkylating agents related to ethylenimines and methylmelamines. These compounds include altretamine, triethylenephosphoramide, triethylenethiophoramide and triethylenemelamine. Additional classes of DNA alkylating agents include the alkyl sulfonates, e.g., busulfan; the azinidines, such as benzodepa; as well as mitoguazone, mitoxantone and procarbazine.

The subject DNA glycosylase inhibitors can also be used for radiosensitization, e.g., to augment radiation therapy and/or photodynamic tumor therapy. The glycosylase inhibitors, by interfering with DNA repair, can be used to enhance radiation damage. In a preferred embodiment, the present invention provides a method for augmenting treatment with ionizing raidiation, e.g., including but not limited to x-rays, and internal and external gamma emitting radioisotopes. In this mode, the subject method can enhance the localization of cytotoxicity of radiation therapy.

The effects of ionizing radiation on living cells generally result in DNA damage and cell death; the effects being proportional to the dose rate. Ionizing radiation has been postulated to induce multiple biological effects by direct interaction with DNA or through the formation of free radical species leading to DNA damage. These effects include gene mutations, malignant transformation, and cell killing. Radiation therapy relies of two types of ionizing radiation: (1) subatomic particle radiation, which consists of alpha particles, beta particles (electrons), neutrons, protons, mesons, and heavy ions, and (2) electromagnetic radiation, which exists as a family of waves of varying frequency, including high-frequency x-rays. Electromagnetic radiation in the form of x-rays is most commonly used in megavoltage radiation therapy to treat common malignant tumors. Gamma rays, a form of electromagnetic radiation similar to x-rays but emitted by radioactive isotopes of radium, cobalt, and other elements, are also commonly used.

In one embodiment, the present invention provides a method of radiation therapy for a host harboring a tumor. The method includes the steps of administering to the host a DNA glycosylase inhibitor of the present invention and administering ionizing radiation to the host in proximity to the tumor. In this manner, the localization of the radiation treatment can be enhanced. The subject glycosylase inhibitors can also be used to generate cells, e.g., in culture, that can be used to ascertain the carcinogenic/mutagenic activity of an agent or environmental condition (such as radiation), or the ability of a test agent to protect against DNA damage. At present, the most widely used cell-based carcinogen/mutagen screening assay is the Ames test.

This assay is described by Maron et al. (1983) *Mutation Research* 113:173. The Ames test utilizes several unique strains of *Salmonella typhimurium* that are histidine-dependent for growth and that lack the usual DNA repair enzymes. The frequency of normal mutations that render the bacteria independent of histidine (i.e., the frequency of spontaneous revertants) is low. The test allows one to evaluate the impact of a compound on this revertant frequency. In contrast to the Ames test, the cells of the present invention can be generated from any organism, and particularly from human cells. Thus, the test cells of the present invention can be better models for the carcinogenic/mutagenic activity of an agent on human cells, removing the need to extrapolate data from a bacterial cell. Briefly, the test cell is generated by contacting it with one or more of the subject glycosylase inhibitors in order to render it at least partially defective for DNA repair. The repair-defective test cell is then contacted with the test agent, or placed under the test conditions. A change in phenotype of the cell can be used to score for mutation, with the frequency of that phenotypic change in the presence of the test agent or condition being compared to its absence. In other embodiments, the cell is contacted with a known carcingoen, and a second agent can be added and its ability to protect against DNA damage is assessed.

In another embodiment, the glycosylase inhibitor can be used to isolate glycosylase enzymes from cell preparations. Briefly, the method comprises contacting a cytoplasmic preparation of a cell with one or more glycosylase inhibitors which has been derivatized to a solid support, e.g., for a period of time sufficient for DNA glycosylases present in the cytoplasmic preparation to bind to the solid support. The support can removed from contact with the cytoplasmic preparation, and accordingly isolates bound DNA glycosylase from the cell preparation. Microsequencing can be carried out on the protein, or antibodies can be raised against the protein, and ultimately used to clone a gene encoding the isolated glycosylase.

IV. PHARMACEUTICAL COMPOSITIONS

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a glycosylase inhibitor of the present invention which is effective for producing some desired therapeutic effect by inhibiting a DNA repair pathway in at least a sub-population of cells in an animal and thereby altering the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject glycosylase inhibitor from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present glycosylase inhibitors may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66.1–19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the glycosylase inhibitor which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a glycosylase inhibitor of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient.

A glycosylase inhibitor of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate, (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered glycosylase inhibitor moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active glycosylase inhibitor, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a glycosylase inhibitor of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active glycosylase inhibitor of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the inhibitor in the proper medium. Absorption enhancers can also be used to increase the flux of the inhibitor across the skin. The rate of such flux can be controlled by either providing a rate controlling membrane or dispersing the inhibitor in a polymer matrix or gel.

Ophthalmic formulations, eye ointments, powders, solutions and the like, are also contemplated as being within the scope of this invention.

Pharmaceutical compositions of this invention suitable for parenteral administration comprise one or more glycosylase inhibitors of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in to the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject glycosylase inhibitors in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Where the subject glycosylase inhibitors are incorporated as part of oligonucleotides, e.g., R2 and/or R3 are one or more nucleotides, the can be administered in a manner similar to that appropriate for antisense therap. For instances, the oligomers of the invention can be formulated for a variety of modes of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Many of the art methods for uptake of oligonucleotides rely on normal mechanisms used by mammalian cells for the uptake and intracellular transport of macromolecules. In preferred embodiments, oligonucleotide delivery systems of the present invention rely on endocytic pathways for the uptake of the subject inhibitors by the targeted cell. Exemplary delivery systems of this type include liposomal derived systems, poly-lysine conjugates, and artificial viral envelopes.

In a representative embodiment, an oligonucleotide construct of the present invention can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, "lipofection" of a cancer cell can be carried out using liposomes tagged with monoclonal antibodies against a cancer-associated antigen (see, Viac et al. (1978) *J Invest Dermatol* 70:263–266; see also Mizuno et al. (1992) *Neurol. Med Chir.* 32:873–876).

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular glycosylase inhibitor of the present invention employed, or the ester, salt or amide thereof, the route of administration, the time of administration, the rate of excretion of the particular compound being employed, the duration of the treatment, other drugs, compounds and/or materials used in combination with the particular inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a glycosylase inhibitor will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active glycosylase inhibitor may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

Exemplification

The invention now being generally described, it will be more readily understood by reference to the following examples which are included merely for purposes of illustration of certain aspects and embodiments of the present invention, and are not intended to limit the invention.

DNA repair enzymes, expressed in all organisms, maintain the integrity of genetic information through reconstitution of DNA damaged by attacks by exogenous and endogenous agents as well as errors that arise during replication. The link between defective DNA repair and a variety of genetic diseases, including cancer, has been established. Furthermore, our understanding of the significance of DNA repair in regulating other critical biological events, such as cell cycle, has been greatly improved. The findings underscore the importance of identifying the structural basis for the target recognition and catalytic activities by DNA repair enzymes. In order to obtain a high resolution picture to address this issue, it is essential to obtain a DNA-protein complex of proper stability for X-ray studies. However, the fleeting nature of the association between the wild type enzyme and its DNA substrate requires modification either on the enzyme or on the substrate to retain a stable complex.

By modifying DNA substrates, we and others have obtained potent inhibitors for a prominent class of DNA repair enzymes, the DNA glycosylases. However, a stable complex formed by a transition state analog and the enzyme is favored over one involving a substrate analog for structural studies addressing the aforementioned mechanistic issues. In addition, the recent success in cloning novel DNA glycosylases from eukaryotic sources using inhibitor-based affinity chromatography has intensified the search for highly specific and potent inhibitors. Given the maximum interaction between the altered substrate and the enzyme in transition state, given the emerging evidence supporting a conserved mechanism for DNA glycosylases of different organisms, transition state analogs of DNA glycosylation hold great promise for providing powerful probes for cloning novel DNA repair enzymes from mammalian sources.

We noted two distinctive features of the proposed transition state structure for DNA glycosylation: 1) Substantial positive charge is accumulated at O-1' and C-1 '; 2) The glycosidic bond between C-1' and the leaving base is substantially extended comparing with substrate (FIG. 1). This proposed transition state structure is supported by the finding that pyrrolidine inhibitors 1, designed to mimic the positively charged ribosyl ring, binds DNA glycosylases with stronger affinity than those of substrate analogs. However, it is found that 1, lacking a base moiety, is a general inhibitor of DNA glycosylases. Here we wish to report the design, synthesis and biochemical evaluation of base containing transition state analogs as inhibitors for DNA glycosylase.

Figure 2:
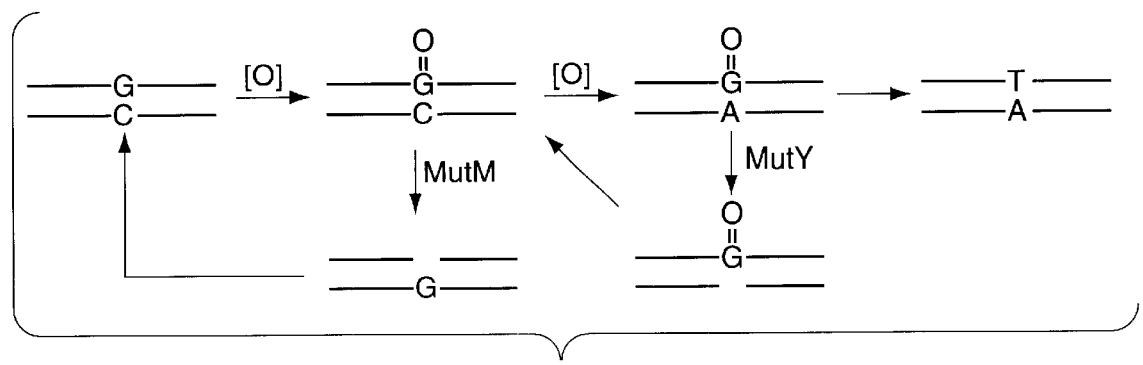
FIG. 2 depicts an exemplary repair pathway involving the bacterial MutY and MutM DNA repair enzymes.

We reasoned that attachment of bases to the pyrrolidine ring with a proper link could lead to inhibitors possessing stronger binding affinities than 1. More importantly, the specificity of the inhibitors could be tailored for different enzymes by introducing different bases into the inhibitor. We decided to introduce a methylene unit to link the base and pyrrolidine ring in our new inhibitor 2. The formal insertion of a $CH_2$ unit into the glycosidic bond not only renders 2 resistant toward glycosylation, but also mimics the extension of the glycosidic bond in transition state. In our initial study, we chose to synthesize the adenine containing inhibitor (2a) for adenine glycosylase MutY. MutY, along with MutM, constitutes a network to defend the bacteria genome against oxidative damage. One of the major substrates for MutY is oxo-G paired opposite A, which is an intermediate along the pathway that resulted in the highly mutagenic G/C to A/T transversion that is initiated by oxidative damage to G residues DNA (FIG. 2).

Figure 3:
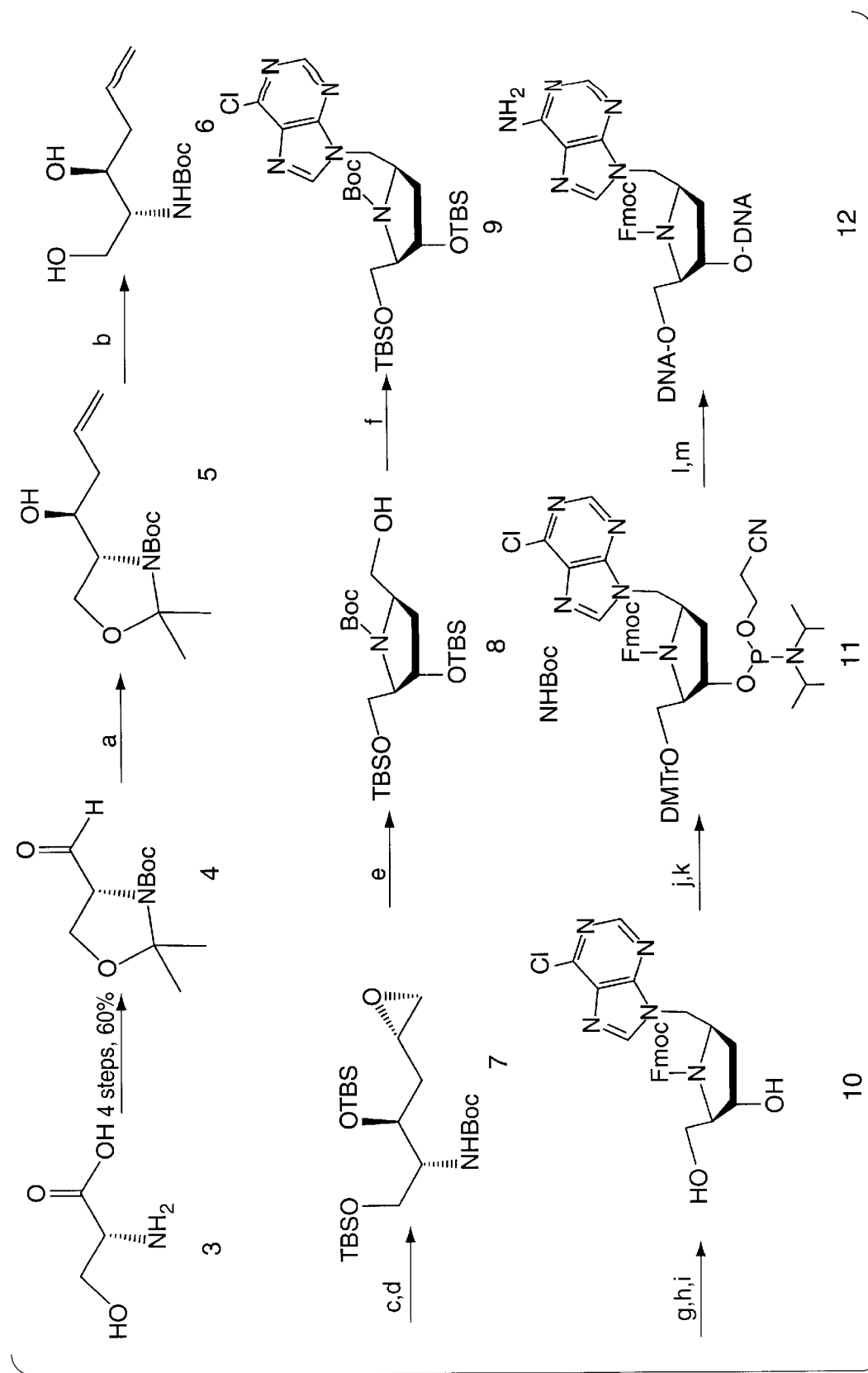
FIG. 3 depicts an exemplary synthesis scheme for an adenosine analog.

The synthesis of inhibitor 2a, as outlined in FIG. 3, starts from the commercially available D-serine (3). Following a recently reported procedure, aldehyde 4 is obtained in 60% overall yield from 3. Diastereoselective allylboration of 4 was accomplished in excellent selectivity (94% de). Deprotection of homo-allylic alcohol 5 furnished the diol 6. Protection of diol 6 as the corresponding disilylether and the subsequent treatment of the olefin with mCPBA in methylene chloride resulted in the formation of the corresponding epoxide as a mixture of diasteremers (5:1) in favor of the desired diastereomer. Intramolecular cyclization of epoxide 7 carried out in acetic acid at room temperature leads to the formation of key intermediate 8 in excellent yield. The substitution of the alcohol by 6-chloropurine was accomplished through a Mitsunobu reaction. Subsequent protecting group manipulations using standard conditions furnished cyclic diol 10. The protection of the pyrrolidine nitrogen with Fmoc group is required for subsequent solid synthesis of DNA. Tritylation of the primary alcohol followed by phosphitylation of the secondary alcohol provided the desired phosphoramidite 11. It should be noted that this route can be readily adapted for the synthesis of other base containing inhibitors.

Phosphararidite 11 was employed for the solid state synthesis of a 25-mer oligonucleotide with a centrally modified base (5'-GGA TAG TGT CCA N GTT ACT CGA AGC-3', N=modified residue, SEQ ID NO:1) and was coupled into the oligonucleotide in high efficiency (>95% yield). The deprotection of the oligonucleotide and the conversion of the 6-chloropurine into adenine was accomplished by incubating with aqueous ammonia at 55° C. The resulting oligonucleotide mixture was concentrated and purified by denaturing polyacrylamide gel electrophoresis to provide the desired single stranded oligonucleotide. The presence of modified residue in the oligonucleotide was confirmed by nucleioside composition analysis. The double strand DNA required for biochemical studies was prepared by 5'-$^{32}$P-end labeling of the oligonucleotide and subsequently annealing to a complementary 25-mer (5'-GCT TCG AGT AAC OG TGG ACA CTA TCC-3', SEQ ID NO: 2) with a OxoG residue paired opposite N.

Figure 4A:
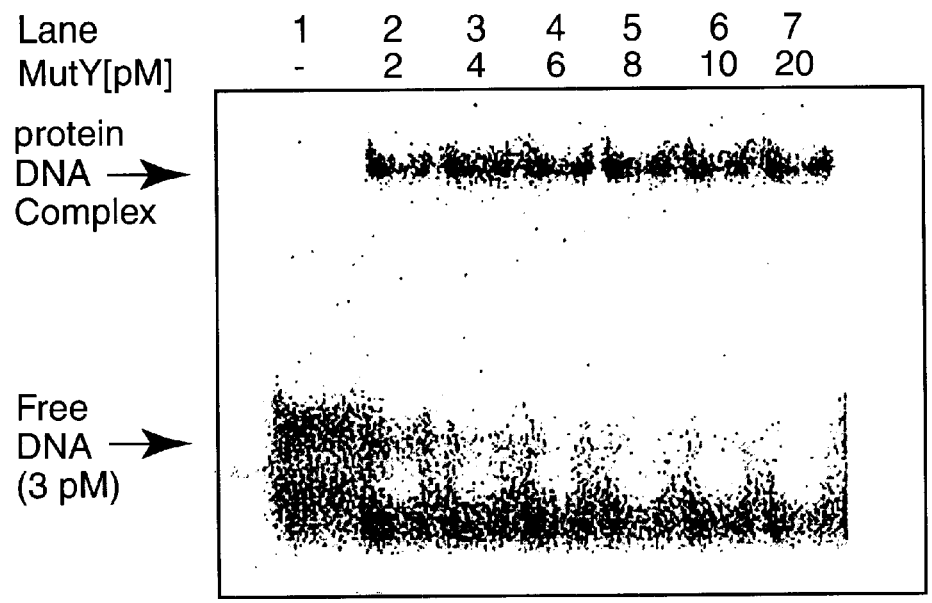
FIGS. 4A, 4B and 5 are gel shift assays.
Figure 4B:
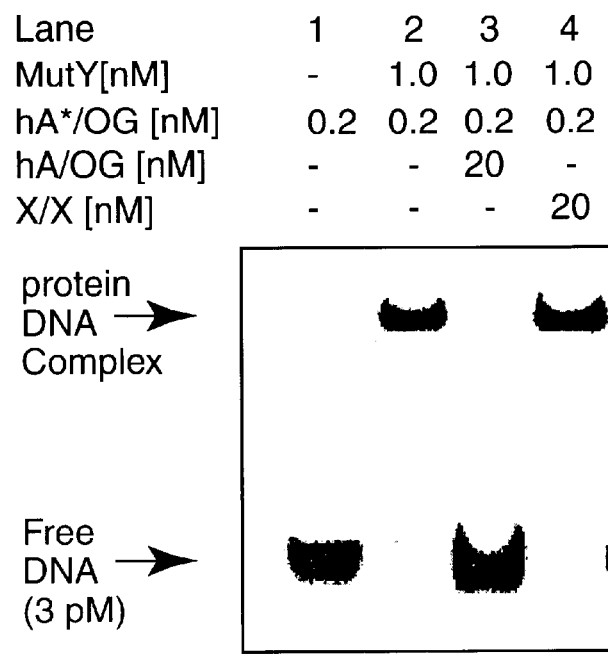
Figure 5:
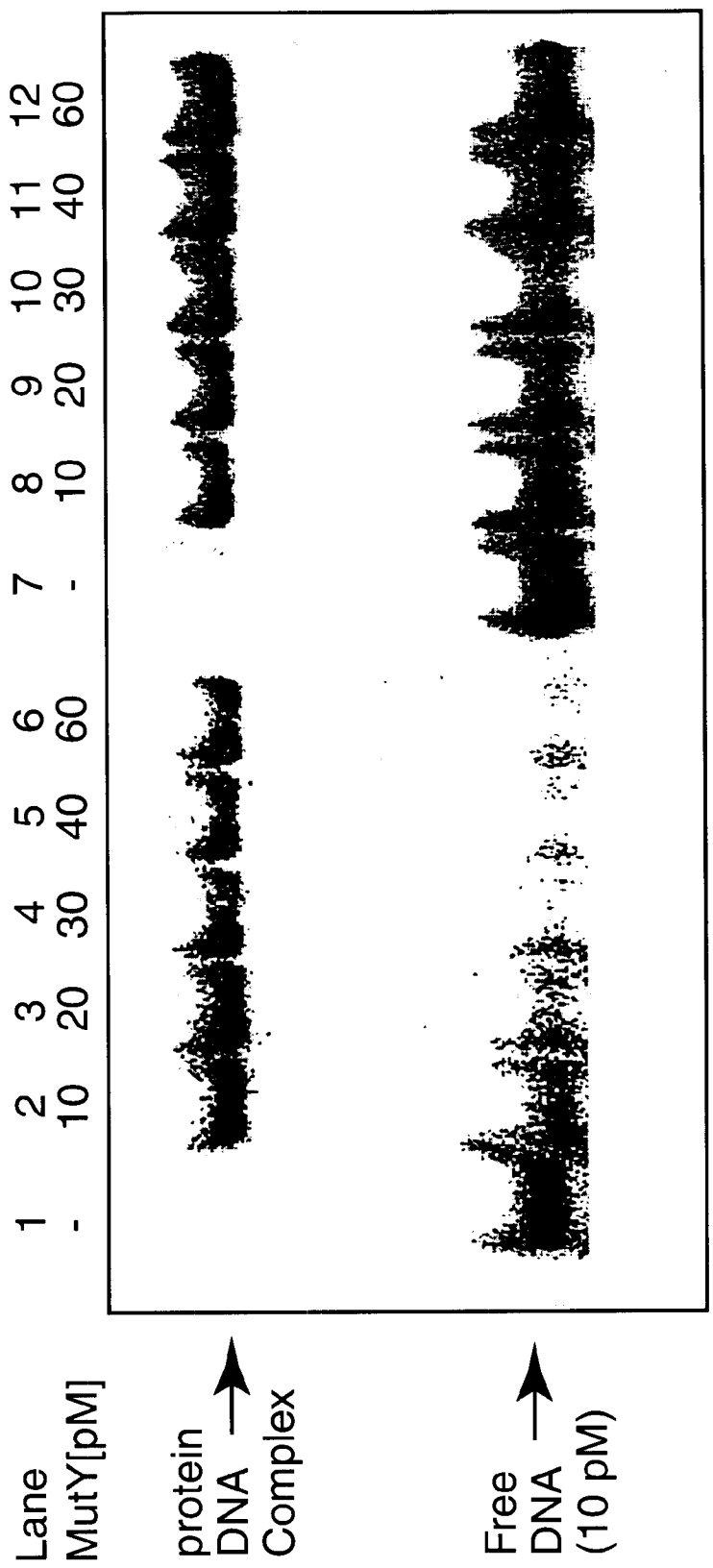

The binding affinity of this singly modified duplex 25-mer toward MutY was investigated by the electrophoretic mobility shift assay (EMSA). The protein bound or unbound radiolabeled DNA have difference mobility and can be readily separated through electrophoresis. Titration of hA containing DNA with increasing concentrations of MutY levels reveals that the inhibitor binds to the protein with extraordinary affinity (FIG. 4A). We estimated the Kd to be lower than 2 pM. This Kd of the adenine containing inhibitor is two orders of magnitude lower than those derived from substrate analogs when MutY was the intended target. It is also one order of magnitude lower than the lowest Kd reported for inhibitors directed toward any DNA glycosylas. Moreover, the inhibitor is recognized specifically by MutY as indicated in competition assay (FIG. 4B). The binding of the $^{32}$P-labeled DNA inhibitor to MutY was abolished in the presence of 100 fold excess of the corresponding unlabeled DNA inhibitor, while it is retained in the presence of 100 fold excess of a double strand DNA of random sequence. We also found that 1 binds to MutY in a dramatically reduced strength (FIG. 5). The Kd for the binding of 1 to MutY is determined to be 65 ±13 pM and therefore is at least 20 times higher than 2a. These results clearly indicate that interactions between the adenine attached to pyrrolidine ring in inhibitor 2a and residues of MutY contribute significantly to the binding strength of the inhibitor.

In summary, we have designed a new class of base containing transition state analogs for DNA repair enzymes. A stereoselective, general, and practical synthetic route has been developed for these inhibitors. More importantly, we have demonstrated that 2a binds MutY protein specifically in a strength that surpassed the best inhibitor previously reported for any glycosylases. The presence of adenine in the inhibitor has been shown to be critical for this extraordinary binding strength. Synthesis and biochemistry studies of other base containing inhibitors are currently underway. We believe that this new class of inhibitors will find wide applications in various aspects of research involving DNA glycosylases including structural studies, isolation and cloning of novel DNA glycosylases as well as development of new therapeutic reagents for cancer treatment.

All of the above-cited references and publications are hereby incorporated by reference.

Equivalents

Those skilled in the art will recognize, or be able to ascertain using no more than routine experimentation, numerous equivalents to the glycosylase inhibitors and methods of use thereof described herein. Such equivalents are considered to be within the scope of this invention and are covered by the following claims.

---

What is claimed is:

1. A compound represented by the formula, or a pharmaceutically acceptable salt thereof:

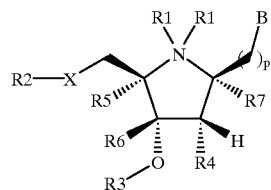

wherein
- B is a nucleoside purine or pyrimidine base, or a heterocyclic analog thereof;
- X is O, N, S or $CH_2$;
- R1, independently for each occurrence, is absent or is a hydrogen, or an amino protecting group;
- R2 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $-(CH_2)_m-R8$, $-(CH_2)_m-OH$, $-(CH_2)_m-O$-lower alkyl, $-(CH_2)_m-O$-lower alkenyl, $-(CH_2)_m-O-(CH_2)_n-R8$, $-(CH_2)_m-SH$, $-(CH_2)_m-S$-lower alkyl, $-(CH_2)_m-S$-lower alkenyl, $-(CH_2)_m-S-(CH_2)_n-R8$, or a solid or polymeric support;
- R3 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $-(CH_2)_m-R8$, $-(CH_2)_m-OH$, $-(CH_2)_m-O$-lower alkyl, $-(CH_2)_m-O$-lower alkenyl, $-(CH_2)_m-O-(CH_2)_n-R8$, $-(CH_2)_m-SH$, $-(CH_2)_m-S$-lower alkyl, $-(CH_2)_m-S$-lower alkenyl, $-(CH_2)_m-S-(CH_2)_n-R8$, or a solid or polymeric support;
- R4, R5, R6 and R7 are each, independently, as valence and stability permit, hydrogen, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $-(CH_2)_m-R8$, $-(CH_2)_m-OH$, $-(CH_2)_m-O$-lower alkyl, $-(CH_2)_m-O$-lower alkenyl, $-(CH_2)_m-O-(CH_2)_n-R8$, $-(CH_2)_m-SH$, $-(CH_2)_m-S$-lower alkyl, $-(CH_2)_m-S$-lower alkenyl, $-(CH_2)_m-S-(CH_2)_n-R8$;
- R8 is, independently for each occurrence, a substituted or unsubstituted aryl, aralkyl, cycloalkyl, cycloalkenyl or heterocycle, a carbonyl, a sulfonyl or a phosphoryl; and
- p is 1 or 2, and n and m are independently for each occurrence zero or an integer in the range of 1 to 6, which compound inhibits an N-glycosidic activity of a DNA glycosylase.

2. A compound represented by the formula, or a pharmaceutically acceptable salt thereof:

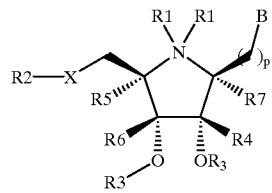

wherein
- B is a nucleoside purine or pyrimidine base, or a heterocyclic analog thereof;
- X is O, N, S or $CH_2$;
- R1, independently for each occurrence, is absent or is a hydrogen, or an amino protecting group;
- R2 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $-(CH_2)_m-R8$, $-(CH_2)_m-OH$, $-(CH_2)_m-O$-lower alkyl, $-(CH_2)_m-O$-lower alkenyl, $-(CH_2)_m-O-(CH_2)_n-R8$, $-(CH_2)_m-$ SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R3 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R4, R5, R6 and R7 are each, independently, as valence and stability permit, hydrogen, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8;

R8 is, independently for each occurrence, a substituted or unsubstituted aryl, aralkyl, cycloalkyl, cycloalkenyl or heterocycle, a carbonyl, a sulfonyl or a phosphoryl; and p is 1 or 2, and n and m are independently for each occurrence zero or an integer in the range of 1 to 6, which compound inhibits an N-glycosidic activity of a DNA glycosylase.

3. A nucleic acid comprising at least one analog represented by the formula:

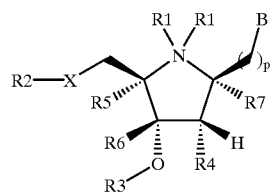

wherein

B is a nucleoside purine or pyrimidine base, or a heterocyclic analog thereof;

X is O, N, S or CH$_2$;

R1, independently for each occurrence, is absent or is a hydrogen, or an amino protecting group;

R2 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R3 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R4, R5, R6 and R7 are each, independently, as valence and stability permit, hydrogen, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8;

R8 is, independently for each occurrence, a substituted or unsubstituted aryl, aralkyl, cycloalkyl, cycloalkenyl or heterocycle, a carbonyl, a sulfonyl or a phosphoryl; and p is 1 or 2, and n and m are independently for each occurrence zero or an integer in the range of 1 to 6, which nucleic acid inhibits an N-glycosidic activity of a DNA glycosylase.

4. A nucleic acid comprising at least one analog represented by the formula:

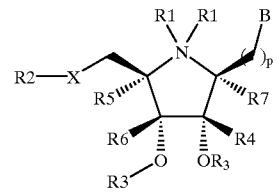

wherein

B is a nucleoside purine or pyrimidine base, or a heterocyclic analog thereof;

X is O, N, S or CH$_2$;

R1, independently for each occurrence, is absent or is a hydrogen, or an amino protecting group;

R2 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonarnido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R3 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R4, R5, R6 and R7 are each, independently, as valence and stability permit, hydrogen, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8;

R8 is, independently for each occurrence, a substituted or unsubstituted aryl, aralkyl, cycloalkyl, cycloalkenyl or heterocycle, a carbonyl, a sulfonyl or a phosphoryl; and p is 1 or 2, and n and m are independently for each occurrence zero or an integer in the range of 1 to 6, which nucleic acid inhibits an N-glycosidic activity of a DNA glycosylase.

5. A glycosylase inhibitor comprising a analog represented by the formula:

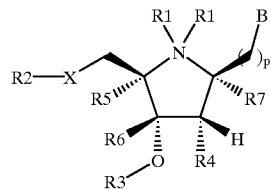

wherein

B is a nucleoside purine or pyrimidine base, or a heterocyclic analog thereof;

X is O, N, S or CH$_2$;

R1, independently for each occurrence, is absent or is a hydrogen, or an amino protecting group;

R2 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R3 is a hydrogen, a nucleotide or oligonucleotide, a phosphoryl, a phosphonate, a phosphoramidate, a carbamate, a phosphorothioate, a phosphorodithioate, a hydroxyl blocking group, or as valence and stability permit, a halogen, a lower alkyl, a lower alkenyl, a lower alkynyl, a carbonyl, a thiocarbonyl, a ketyl, an aldehyde, an amino, an acylarmino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or a solid or polymeric support;

R4, R5, R6 and R7 are each, independently, as valence and stability permit, hydrogen, a halogen, a lower alkyl, a lower alkenyl, a lower alkynyl, a carbonyl, a thiocarbonyl, a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8;

R8 is, independently for each occurrence, a substituted or unsubstituted aryl, aralkyl, cycloalkyl, cycloalkenyl or heterocycle, a carbonyl, a sulfonyl or a phosphoryl; and p is 1 or 2, and n and m are independently for each occurrence zero or an integer in the range of 1 to 6, which inhibitor inhibits an N-glycosidic activity of a DNA glycosylase.

6. A glycosylase inhibitor, comprising a compound of claim 1 or 2.

7. The compound of claim 1 or 2, the nucleic acid of claim 3 or 4, or the inhibitor of claim 5 or 6, wherein the DNA glycosylase is a member of the EC category EC 3.2.2.

8. The compound of claim 1 or 2, wherein the DNA glycosylase is selected from the group consisting of a purine nucleosidase (EC 3.2.2.1), an inosine nucleosidase (EC 3.2.2.2), a uridine nucleosidase/uracil deglycosylase (EC 3.2.2.3), a ribosylpyrimidine nucleosidase (EC 3.2.2.8), an inosinate nucleosidase (EC 3.2.2.12), a 1-methyladenosine nucleosidase (3.2.2.13), a dna-deoxyinosine glycosidase (EC 3.2.2.15), a methylthioadenosine nucleosidase (EC 3.2.2.16), a DNA-3-methyladenine glycosidase (I) (EC 3.2.2.20), a DNA-3-methyladenine glycosidase (II) (EC 3.2.2.21), and a formamidopyrimidine-DNA glycosidase (EC 3.2.2.23).

9. The compound of claim 1 or 2, wherein the DNA glycosylase is a mammalian DNA glycosylase selected from the group of MYH, Mpg, 3 Mg, Ung1 and Ung2.

10. The compound of claim 1 or 2, wherein the DNA glycosylase is a bacterial DNA glycosylase selected from the group of MutM, MutT, fpg4 and MutY.

11. The compound of claim 1 or 2, wherein the DNA glycosylase is a viral DNA glycosylase from an Epstein Barr Virus or Herpes Simplex Virus.

12. The compound of claim 1 or 2, which inhibits a glycosylase activity of a bacterial, fungal or viral DNA glycosylase with a Ki at least one order of magnitude less than a human DNA glycosylase of similar specificity.

13. The compound of claim 1 or 2, wherein B is selected from the group consisting of adenine, guanine, thymine, cytosine, uracil and hypoxanthine, or a derivative thereof.

14. The compound of claim 1 or 2, wherein B is a purine or pyrimidine base analog selected from the group consisting of $N^6$-benzoyladenine, $N^2$-isobutyrylguanine, $N^4$-benzoylcytosine, $N^6$-di-n-butylformamidinyladenine, $N^6$-(N-methyl-2-pyrrolidineamidinyl)-adenine, $N^6$-succinyladenine, $N^6$-phthaloyladenine, $N^6$-dimethylacetamidinyladenine, $N^2$-di-n-butylformamidinylguanine, isocytosine, xanthine (3,7-dihydro-1H-purine-2,6-dione), 6-chloropurine, 6-chloro-2-fluoropurine, 2,6-diaminopurine, 2-fluoro-$N^6$-hydroxyadenine, 2,6-dihydroxyaminopurine, 8-bromoadenine, 2-chloroadenine, 8-azidoadenine, 8-mercaptoadenine, 8-aminoadenine, 6-thioguanine, 2,6-dichloropurine, N,N-dimethyl-6-aminopurine, $N^6$-benzyladenine, 1,3-dimethylxanthine, 2-amino-6,8-dihydroxypurine, 6-methoxypurine, 6-mercaptopurine, 6-(2-hydroxyethyl)-aminopurine, $N^6$-(2-isopentyl)-adenine, $N^6$-furfuryladenine (kinetin), 5-bromomethyluracil, 5-dibromomethyluracil, 5-hydroxymethyluracil, 5-formyluracil, 5-fluorouracil, 5-bromouracil, 6-methyl-2-thiouracil, 5-hydroxymethyl-6-methyluracil, 5-hydroxyuracil (isobarbituric acid), 5-methoxyuracil, 5-methylcytosine, 5-trifluoromethyluracil, 5-nitrouracil, 5-aminouracil, 2-thiocytosine, 2-amino-4,6-dihydroxypyrimdine, 4-amino-2,6-dihydroxypyrimidine, 2-amino-4-hydroxy-6-methylpyrimidine, 4-amino-6-hydroxy-2-mercaptopyrimidine.

15. The compound of claim 1 or 2, whrein B is an substituted or unsubstituted heterocycle selected from the group consisting of imidazole, indole, benzimidazole, indazole, pyrazole, benzotriazole, 8-azaadenine, 8-azaguanin, 6-azathymin, 6-azauracil, 5-azacytosine, 8-azahypoxanthine, pyrazolopyrimidine, 3-deazauracil, orotic acid (2,6-dioxo-1,2,3,6-tetrahydro-4-pyrimidine carboxylic acid), barbituric acid, uric acid, ethenoadenine, and allopurinol (4-hydroxy-pyrazolo [3,4-d]pyrimidine).

16. The compound of claim 1 or 2, wherein B is a heterocyclic analogue of a nucleoside base.

17. The compound of claim 1 or 2, wherein R1 is a protecting group selected from the group consisting of aromatic urethane-type protecting groups, aliphatic urethane-type protecting groups, and cycloalkyl urethane-type protecting groups.

18. The compound of claim 1 or 2, wherein one or both of R2 and R3 are hydroxyl-protecting groups selected from the group consisting of a lower alkylsilyl group, a lower alkoxymethyl group, a tetrahydropyranyl group, an aralkyl group, and an acyl group.

19. The nucleic acid of claims 3 or 4, which inhibits an N-glycosidic activity of a DNA glycosylase.

20. The nucleic acid of claim 3 or 4, wherein the nucleic acid is at least 4 nucleotide units in length.

21. The nucleic acid of claim 3 or 4, wherein the nucleic acid is at least 10 nucleotide units in length.

22. A pharmaceutical preparation, comprising the compound of claim 1 or 2; and a pharmaceutically acceptable carrier.

23. A solid support derivatized with a compound of claim 1 or 2, or the nucleic acid of claim 3 or 4.

24. A pharmaceutical preparation, comprising the nucleic acid of claim 3 or 4; and a pharmaceutically acceptable carrier.

25. A pharmaceutical preparation, comprising the inhibitor of claim 5 or 6; and a pharmaceutically acceptable carrier.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(ix) FEATURE:
        (A) NAME/KEY: modified_base
        (B) LOCATION: 13

(xi) SEQUENCE DESCRIPTION: SEQ ID NO:1:

GGATAGTGTC CANGTTACTC GAAGC                      25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single

```
        (D) TOPOLOGY: linear (ii) MOLECULE TYPE: other nucleic acid
        (A) DESCRIPTION: /desc = "oligonucleotide"

(ix) FEATURE:
        (A) NAME/KEY: modified_base
        (B) LOCATION: 13
        (D) OTHER INFORMATION: /mod_base= OTHER
            /note= "OxoG residue paired opposite N"

(xi) SEQUENCE DESCRIPTION: SEQ ID NO:2:

GCTTCGAGTA ACNTGGACAC TATCC                                25
```